United States Patent
Rajala et al.

(10) Patent No.: US 11,083,085 B2
(45) Date of Patent: Aug. 3, 2021

(54) SYSTEM FOR TRANSMITTING ELECTRICAL SIGNALS

(71) Applicant: Clothing Plus MBU Oy, Kankaanpaa (FI)

(72) Inventors: Saara Rajala, Tampere (FI); Manu Myry, Kolkki (FI); Helena Ritamäki, Siuro (FI)

(73) Assignee: Clothing Plus MBU Oy, Kankaanpaa (FI)

( * ) Notice: Subject to any disclaimer, the term of this patent is extended or adjusted under 35 U.S.C. 154(b) by 0 days.

(21) Appl. No.: 16/647,084

(22) PCT Filed: Sep. 13, 2018

(86) PCT No.: PCT/FI2018/050657
§ 371 (c)(1),
(2) Date: Mar. 13, 2020

(87) PCT Pub. No.: WO2019/053330
PCT Pub. Date: Mar. 21, 2019

(65) Prior Publication Data
US 2020/0260578 A1 Aug. 13, 2020

(30) Foreign Application Priority Data
Sep. 14, 2017 (FI) .................... 20175818

(51) Int. Cl.
*H05K 1/02* (2006.01)
*H01R 13/627* (2006.01)
(Continued)

(52) U.S. Cl.
CPC ....... *H05K 1/0283* (2013.01); *H01R 13/6278* (2013.01); *H05K 1/0393* (2013.01);
(Continued)

(58) Field of Classification Search
CPC .......................................... H05K 1/0277–0283
See application file for complete search history.

(56) References Cited

U.S. PATENT DOCUMENTS 9,418,927 B2 * 8/2016 Axisa .................. H01L 23/4985
2008/0257589 A1 10/2008 Ostmann et al.
(Continued)

FOREIGN PATENT DOCUMENTS

| EP | 2679107 A1 | 1/2014 |
| WO | 2011038103 A1 | 3/2011 |
| WO | 2017013493 A1 | 1/2017 |

*Primary Examiner* — Jeremy C Norris
(74) *Attorney, Agent, or Firm* — Young Basile Hanlon & MacFarlane, P.C.

(57) ABSTRACT

A flexible and/or stretchable structural system for transmitting electrical signal between first and second rigid portions comprises a body structure and said first and second portions arranged to said body structure. The modulus of elasticity of said first portion is lower than the corresponding modulus of elasticity of said second portion. In addition the modulus of elasticity of said body structure is lower than the corresponding modulus of elasticity of said second portion. The system comprises also an interface portion, such as e.g. an electrically conducting fabric, textile or knit, which is arranged to said body structure and between said first and second portions. The interface portion electrically connects said first and second portions. The modulus of elasticity of said interface portion is lower than the corresponding modulus of elasticity of said second portion.

19 Claims, 2 Drawing Sheets

(51) Int. Cl.
*H05K 1/03* (2006.01)
*H05K 1/09* (2006.01)
*A41D 1/00* (2018.01)
*A61B 5/00* (2006.01)

(52) U.S. Cl.
CPC ............ *H05K 1/092* (2013.01); *A41D 1/005* (2013.01); *A61B 5/6833* (2013.01); *A61B 2562/166* (2013.01); *A61B 2562/227* (2013.01); *H05K 2201/10151* (2013.01); *H05K 2201/10189* (2013.01)

(56) References Cited

U.S. PATENT DOCUMENTS

| | | |
|---|---|---|
| 2012/0052268 A1 | 3/2012 | Axisa et al. |
| 2014/0206210 A1 | 7/2014 | Ritner |
| 2014/0240932 A1 | 8/2014 | Hsu |
| 2014/0343390 A1 | 11/2014 | Berzowska et al. |
| 2017/0181275 A1 | 6/2017 | Dias et al. |

* cited by examiner

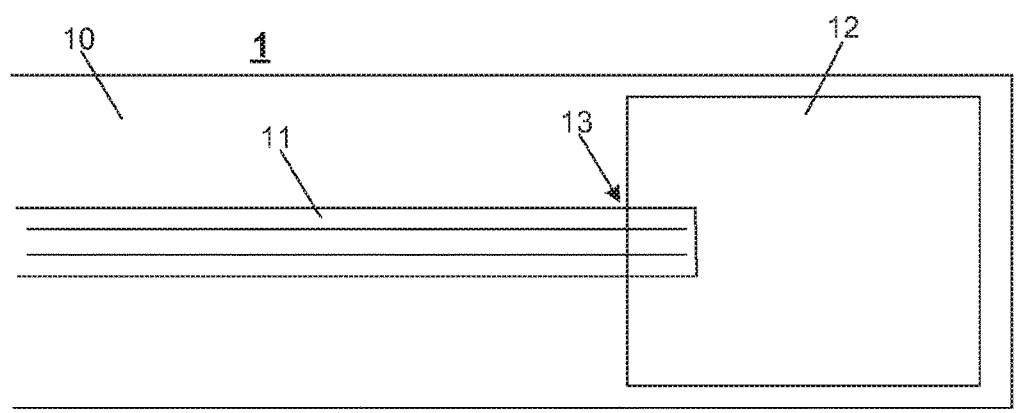
FIG. 1 – PRIOR ART
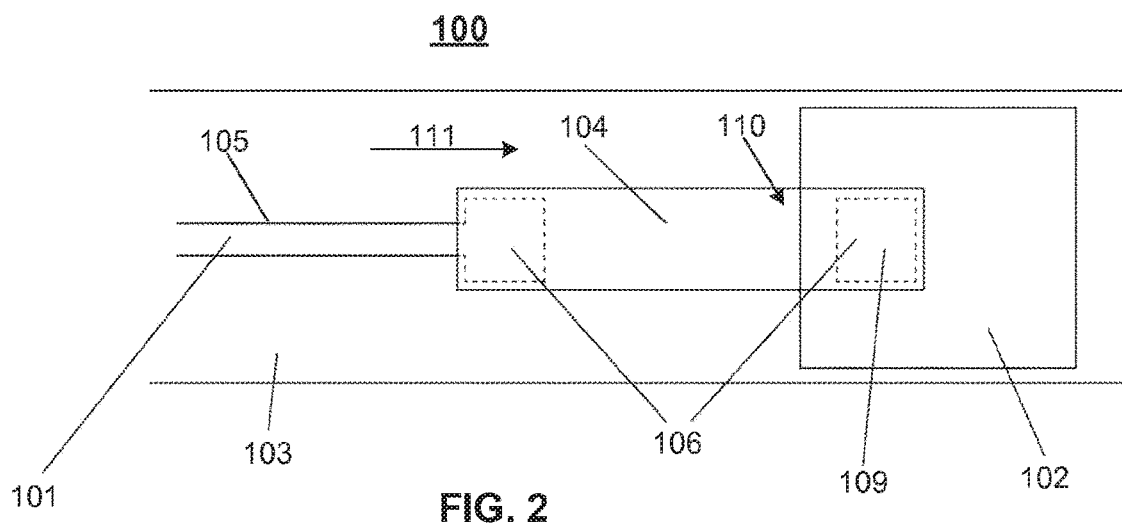
FIG. 2
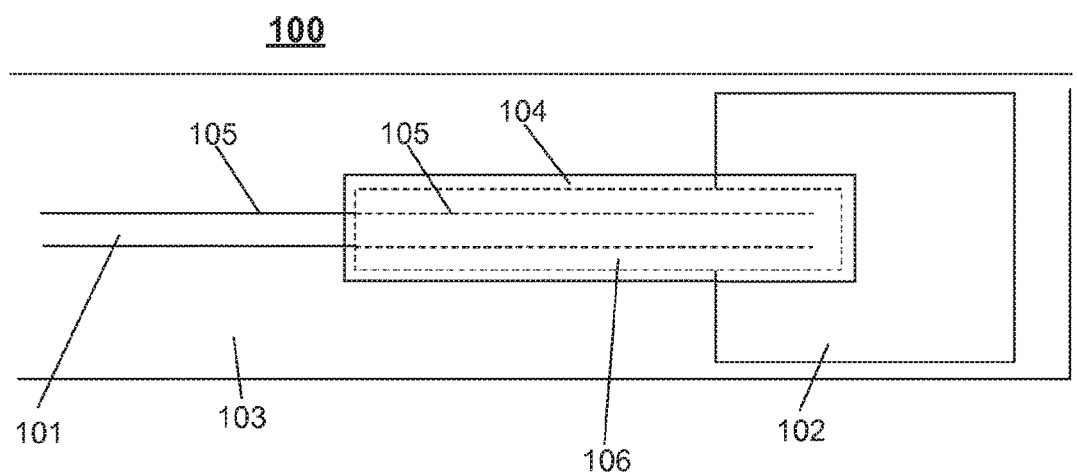
FIG. 3

SYSTEM FOR TRANSMITTING ELECTRICAL SIGNALS

CROSS REFERENCE TO RELATED APPLICATION

The present application claims priority to Finnish Patent Application No. 20175818, filed Sep. 14, 2017, incorporated herein in its entirety.

TECHNICAL FIELD

Embodiments of the invention relate to a flexible and/or stretchable structural system for transmitting electrical signals between different ends or portions, where the different ends or portions have different modulus of elasticity of the material, such as different flexibility and/or stretchability, between a flexible and/or stretchable sensor or conductor and a rigid electric unit, such as a rigid printed circuit board.

BACKGROUND

Flexible and stretchable devices having also rigid areas or components for transmitting signals between two ends are known. Prior art FIG. 1 shows a system 1 that has a flexible substrate 10, a printed wire 11 and a component 12. The component 12 is much more rigid than the flexible substrate 10 and the printed wire 11, which causes a discontinuity point 13 or points in the area between the component 12 and the flex substrate 10. In particularly the printed wires 11 on the flex substrate 10 tend to break from discontinuity points 13, so in particularly at the points where the wires are physically coupled with a rigid component 12. One especially problematic place is between a rigid portion or component island(s) and electrically conducting trace(s), such as e.g., printed wires on a flex circuit board.

The printed wire or other conductor may be connected to a flexible printed circuit board by a rigid snap connection. The snap connection to the flexible printed circuit board or to other flexible print trace or conductor is problematic, as the rigid snap tends to break the print. The snap needs to have high enough pressure in order to conduct the signal from the traces or conductors, such as from the printed wires or traces, to a rigid component, like a transmitter. This causes an area around the snap where the pressure changes from high to low and where the circuit board's ability to bend changes. Additionally, if the snap attaches slightly sideways to the print, the edge of the snap plate can carve into the print either during attachment or later in use.

SUMMARY

Embodiments of the invention alleviate and eliminate the problems relating to the known prior art. Embodiments of the invention provide a system for transmitting electrical signals between different first and second ends or portions having different modulus of elasticity, such as different flexibility and/or stretchability characteristics between a sensor or conductor and an electric unit such as a rigid printed circuit so that the electrical connection between said different end portions can be ensured even if the conductor will break at some point, especially near the rigid component.

The invention relates to a flexible and/or stretchable structural system for transmitting electrical signal between first and second portions according to claim 1.

According to embodiments of the invention a flexible structural system comprises a body structure, where the first and second portions are arranged. The body structure comprises advantageously a flexible and/or stretchable substrate, such as textile or fabric, polymer, PET (polyethylene terephthalate) or polyimide material.

The first portion may be an electrically conductive trace or conductor, such as a printed trace or conductor or electrically conductive ink. One example is a copper wire or etched copper trace, where the etched copper trace is achieved by etching a suitable electrically connecting trace from a copper base material, like a copper sheet or film. The second portion may be a printed circuit board (like an FR4 grade printed circuitry board (PCB), for example), an electrical component, a connector, such as a snap connector (e.g. a snap fastener element) or a rigid connector to the printed circuit board or other rigid electrical component, for example.

According to embodiments of the invention the system comprises also an interface portion arranged to the body structure and in the connection with the first and second portions. The interface portion is configured to electrically connect the first and second portions to each other or number of first and second portions to each other. The interface portion is arranged between the first and second portions, such as, e.g., on top of one or both of them, or overlapping at least partially said first and second portions especially at an area around the second rigid portion, where the flexibility and/or stretchability and/or other modulus of elasticity of the structure changes from low to high (or vice versa) due to different modulus of elasticity of said first and second portions. Thus, even if the first portion, such as a conductor wire or trace, will break or the conductivity of which is compromised at the sensitive area near the second portion, the electric contact can be ensured and secured by the interface portion between the first and second portions. In addition costs of production as well as technical challenges in manufacturing process can also be kept low and easy by using the interface portion. For example attaching of the components to the body structure is not so demanding, because the interface portion will ensure and secure the electric contact between the first and second portions even if the first portion would not extend completely to the area of the second portion.

It is to be noted that the first and second portions may be physically separated portions so that the first portion, like a printed conductor, is finished or ended on the body structure outside the rigid part area of the second rigid portion, whereupon the interface portion is used between the first and second portions as an electrically conductive bridge. However, there is no need to stop the first portion outside the sensitive rigid part area of the second portion, but the first and second portions can also be physically connected to each other. For example, the print conductor (as the first portion) can be continued all the way to the rigid part area of the second portion or into the connection with the second portion (even overlapping with the second portion), especially when the interface portion, such as a conductive fabric, is laminated or the like on top of the conductive print conductor so that it overlaps the sensitive rigid part area of the second portion.

In embodiments of the invention the interface portion comprises an electrically conductive fabric, woven or knit fabric, textile, carbon nanotubes or polymer. For example, the interface portion may include a thermoplastic polyurethane (TPU) or silicone or silicone based material, or electrically conductive ink. Such a material may be very durable for bending and stretching. In embodiments of the invention the first portion, such as printed conductor, can be made by printing a first electrically conductive ink upon the body structure, and the interface portion can be made by printing a second electrically conductive ink upon the body structure. The first and second conductive inks may have different properties, especially different modulus of elasticity. For example the second ink may be more elastic, flexible and/or stretchable than the first ink. In embodiments of the invention the first ink may take the form of 5064H (made by DuPont), and the second ink may take the form of ECM C1-1036 or DuPont PE671 or PE873, for example.

The interface portion may be arranged in the connection of the first and second portions. As an example the interface portion can be laminated, glued, printed or molded, such as molded of a material that has electrically conductive properties. According to an embodiment of the invention the interface portion can be electrically coupled with the first and/or second portions by an adhesive, such as with non-conductive adhesive (NCA) or conductive film or conductive adhesive, such as an anisotropic film (ACF), isotropic film (ICF) or isotropic adhesive (ICA)). When using NCA, the interface portion and/or first and/or second portions may have a textured surface. Such a textured surface penetrates thought the non-conductive adhesive thereby enabling electric contact between the interface portion and the first and/or second portions.

The system may additionally comprise first and second cover portions. The first portion and the interface portion may be arranged between the first and second cover portions. Such a configuration may improve mechanically as well as electrically protecting the first portion and the interface portion. The cover portions may comprise a fabric substrate and cover fabric, such as tricot or Lycra® and Gore-Tex® or compression shirt fabric or polyester, respectively, for example.

The interface portion may be selectively conductive, such as comprising embroidered conductive areas or conductive areas embroidered to the non-conductive fabric or to the first and second cover portions of the system. For example a partly conductive fabric can be used, where the conductive fabric has plural conductive portions electrically separated from each other. By this a plural of conductive interface portions can be manufactured by once or at the same time due to plural of said conductive portions.

In embodiments of the invention the interface portion can be arranged between the first and second portions or on the top or over the portions in order to overlap and extend the sensitive edge area around the second rigid portion. Such a configuration may help ensure and secure the electric conductivity between the first and second portions even if the first portion will break, because the electrically conductive interface portion will extend over the damaged first portion. According to embodiments of the invention the interface portion may be wider than the first portion in order to help ensure and secure the electric conductivity between the first and second portions.

According to embodiments of the invention the second portion may be positioned between two or more first portions, whereupon the interface portion may be used between the two or more first portions and overlapping the second portion. Such a configuration may be suitable where there is a seam or joint area as the rigid second portion and the interface portion is used as an electrically conductive bridge over the rigid second portion and between the two or more first portions, thereby securing the electric connection between at least the two or more first portions, for example.

In addition, it is to be noted that in embodiments of the invention:
  the modulus of elasticity, such as related to flexibility and/or stretchability of the first portion may be lower (being more flexible or elastic) than the corresponding modulus of elasticity of the second portion (more stiffer);
  the modulus of elasticity, such as related to flexibility and/or stretchability of the body structure may be lower (being more flexible or elastic) than the corresponding modulus of elasticity of the second portion (more stiffer); and/or
  the modulus of elasticity, such as related to flexibility and/or stretchability of the interface portion may be lower (being more flexible and elastic) than the corresponding modulus of elasticity of the second portion (more stiffer) or even lower than the corresponding modulus of elasticity of the first portion, which may further improve the electro-mechanical durability of the interface portion.

The flexibility and stretchability relate to or can be measured e.g. by modulus of elasticity of the material [measured, e.g., by $N/m^2$]. A "greater modulus of elasticity" corresponds to greater stiffness/rigidity, and is defined as an object's or substance's resistance to being deformed elastically (i.e., non-permanently) when a stress is applied to it (a stiffer material will have a higher modulus of elasticity).

Embodiments of the present invention may provide improved electrical coupling and connection between a printed wire conductor and a rigid component is achieved, even if the conductor will break at some point, especially at the sensitive area near or around the rigid component, as is discussed elsewhere in this document. In embodiments of the invention This may be achieved by the interface portion, which may be easy, fast and inexpensive to manufacture and integrate to product structure of for example any wearable product, such as a clothing.

The exemplary embodiments presented in this text are not to be interpreted to pose limitations to the applicability of the appended claims. The verb "to comprise" or "include" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which:
FIG. 1 illustrates an example of a prior art device;
FIGS. 2-3 illustrate principles of an exemplary system for transmitting electrical signal between first and second portions according to an advantageous embodiment of the invention.

DETAILED DESCRIPTION

Figure 4:
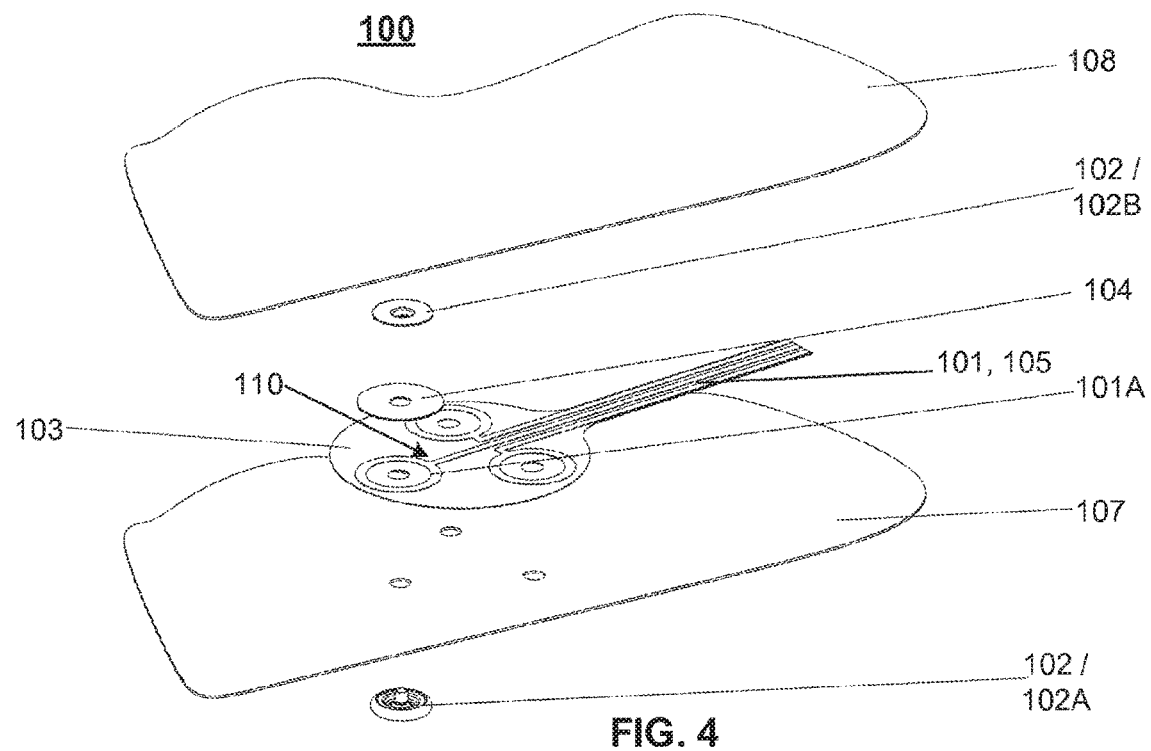
FIG. 4 illustrates an exemplary system for transmitting electrical signal between first and second portions according to an advantageous embodiment of the invention.

FIG. 1 illustrates an example of a prior art device, and it is discussed in more details already in connection with the background portion above.

FIGS. 2-6 illustrate exemplary embodiments of a flexible structural system 100 for transmitting electrical signals between first and second portions 101, 102. In the illustrated embodiments system 100 comprises a body structure 103 to which the first portion 101 and second portion 102 are arranged. For example, portions 101, 102 may be laminated to the body structure 103 or even together, but also other methods can be used. The first portion 101 may take the form of an electrically conductive printed conductor 101, such as electrically conductive ink, such as DuPont 5064H. First portion 101 may take the form of a copper wire or etched copper trace. Such a trace may be formed by etching a suitable electrically connecting trace from a copper base material, like a copper sheet or film. The second portion 102 may take the form of a rigid printed circuit board (like grade FR4 PCB, for example), or other rigid component, such as a snap connector (an example of which is depicted in more details in FIG. 4).

The interface portion 104 may be arranged to the body structure 103 so that it electrically connects the printed conductor 101 and the rigid component 102. The interface portion 104 may be e.g. laminated to the body structure but also other methods described in this document can be used. In FIG. 2 the printed conductor 101 does not extend to the rigid component 102 but is finished outside the rigid component 102. In FIG. 2 the interface portion 104 is arranged between the printed conductor 101 and the rigid component 102 overlapping at least partially the printed conductor 101 and the rigid component 102, particularly at a sensitive area 110 around the printed conductor 101 and the rigid component 102. In that point or area the flexibility and/or stretchability of the structure changes from high to low in at least direction 111. This is mainly due to different modulus of elasticity of the printed conductor 101 and the rigid component 102 or as well of the body structure 103 and the rigid component 102. Reference 109 denotes a contact pad on the rigid component 102 with which the interface portion 104 is coupled.

As can be seen in FIG. 3 the printed conductor 101 and the rigid component 102 can also be physically connected to each other. In the exemplary embodiments depicted in FIGS. 2 and 3 the interface portion 104 is electrically coupled with the printed conductor 101 and the rigid component 102, and also to the body structure 103 by an adhesive 106, such as by an ACF film and conductive PSA tape, or electrically conductive epoxy, for example. In the embodiments of FIGS. 2-3 the interface portion 104 is wider than at least printed conductor 101 in order to better ensure and secure the electric conductivity between the printed conductor 101 and the rigid component 102, although alternative configurations and relative widths may be used.

In certain embodiments the flexibility and/or stretchability of the printed conductor 101 may be greater than the flexibility and/or stretchability of the rigid component 102. The flexibility and/or stretchability of the body structure 103 may be greater than the flexibility and/or stretchability of the rigid component 102. The flexibility and/or stretchability of the interface portion 104 may be greater than the flexibility and/or stretchability of the rigid component 102, or even greater than the flexibility and/or stretchability of the printed conductor 101. The flexibility and/or stretchability are here only examples of modulus of elasticities.

FIG. 4 illustrates a perspective view of an exemplary system 100 for transmitting electrical signals between first and second portions 101, 102 according to an embodiment of the invention. In the illustrated embodiment of FIG. 4, the first portion 101 may take the form of printed conductor 101, 105, or another type of conductor, such as a copper wire or the like. Second portion 102 may take the form of a snap connector 102 or snap electrode 102A, 102B having a cap portion 102A and the counterpart portion 102B (hereafter referred as a snap, which may be made of a steel, and have a shape of circular plate with a protrusion portion, as is described in Figures, for example). Interface portion 104 is shown as a circular portion 104, which has greater diameter than the snap 102 and the end portion 101A of the printed conductor 101, 105 so that the interface portion 104 still extends over the printed conductor 101, 101A, 105 (as the first portion) and also over the snap 102, 120A, 102B (as the second portion). Such a configuration may better ensure electrical connection between the printed conductor 101, 101A, 105 and snap 102. The circular interface portion 104 can also be other form, such as an oval or rectangle.

In certain embodiments of the invention portion 104 may nonetheless extend over the printed conductor 101, 101A, 105 and also over the snap 102, 120A, 102B. Circular interface portion 104 may take the form of an electrically conducting material, such as fabric or textile or knit or other material, like conductive polymer like TPU, for example. Portion 104 can also be attached or coupled to the body structure 103 and in connection with the printed conductor 101, 101A, 105 and snap 102, such as by using lamination or gluing or mechanically punching or by using other techniques described in this document.

In the embodiment of FIG. 4 the snap may be punched through the body structure 103 and the interface portion 104. In the embodiment of FIG. 4, snap 102 is arranged in connection with the printed conductor 101, 101A, 105.

The system 100 depicted in FIG. 4 comprises also first and second cover portions 107, 108 in order to mechanically as well as electrically protect the printed conductor 101, 101A, 105 and the interface portion 104. Such a cover may also overlap and analogously protect portions 102B of snap 102.

In embodiments of the invention portion 104 may take the form of a short trace of conductive knit. In such a configuration printed trace 101, 105 can be moved away from the snap 102 and the electric contact is led by the short trace of conductive knit. This may provide for more uniform bending and pressure on the printed traces 101, 105 as without the short trace of conductive knit as said interface portion 104, which may provide improved breaking resistance. Referring now to the sensitive area 110 between the soft/elastic/stretchable body structure 103 and (more) rigid component 102 and transmitting signals with between the rigid component 102 and the printed traces 101, 105. In the sensitive area 110 the printed conductor 101, 105 will more easily break on stretch and bending than in other areas.

Interface portion 104 may take the form of an electrically conductive, flexible, beneficially stretchable, mechanically durable, typically woven or knit fabric, but could be non-woven as well, could be embroidered on fabric and potentially made of conductive polymer like TPU or silicone. In addition portion 104 may be ink-like, such as an extra elastic layer printed on top of the first portion 101, such as for example elastic ink printed on or at least substantially aligned with the sensitive area 110. In certain embodiments the extra conductive layer 104, such as conductive polymer, may be also overmolded on top of the first portion 101.

Figure 5:
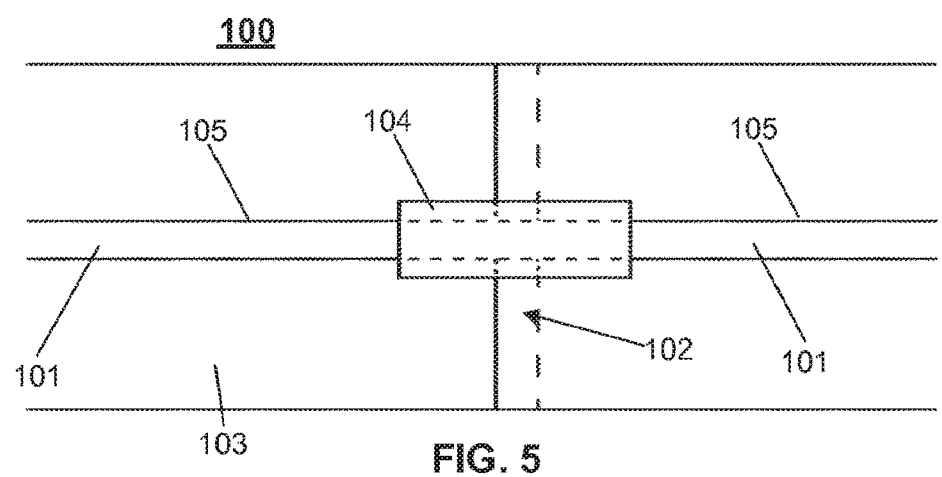
FIG. 5 illustrates an exemplary system for transmitting electrical signal between two first portions and over a second portion according to an advantageous embodiment of the invention.

FIG. 5 illustrates an exemplary embodiment of a system 100 for transmitting electrical signals between two first portions 101 arranged on the body structure 103. In the embodiment of FIG. 5 second portion 102 is positioned between the two first portions 101. In the embodiment depicted in FIG. 5 the second portion 102 takes an exemplary form of a seam or joint area. The interface portion 104 is arranged to extend over the more rigid seam or joint area 102, thereby better ensuring and securing electric connectivity between printed conductors 105 of the first portions 101 and over the second portion 102. For example the body structure 103 may be a piece of a clothing, for example, whereupon the seam or joint area 102 may be arranged in a piece of clothing where different movements will cause bending and stretching and thereby stress in the area around the seam or joint area 102, which may otherwise cause fracture to or breakage of the conductors 105.

Figure 6:
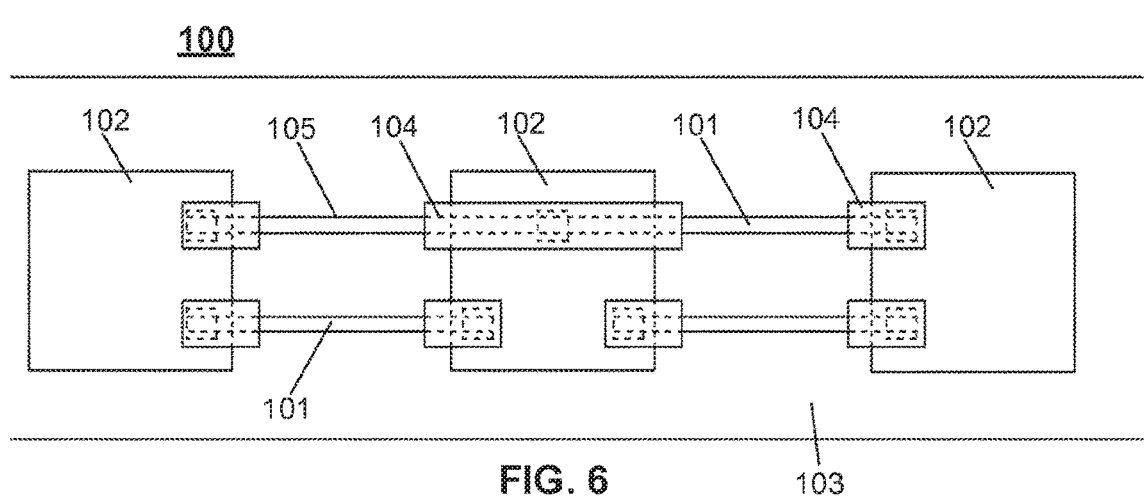
FIG. 6 illustrates an exemplary system for transmitting electrical signal between and over two or more first and second portions according to an advantageous embodiment of the invention.

FIG. 6 illustrates an embodiment of a system 100 for transmitting electrical signals between and over two or more first 101 and second 102 portions arranged on the body structure 103. According to the embodiment of FIG. 6 interface portion 104 may be arranged between the first and second portions 101, 102 correspondingly as is depicted in FIGS. 2 and 3, for example. In addition to this (or alternatively in additional embodiment) the second portion 102 may be positioned between two or more first portions 101, whereupon the interface portion 104 is used between the two or more first portions 101 and overlapping the second portion 102. Such an interface portion 104 also electrically couples the second portion 102 with the conductors 105 of the first portions 101 in the illustrated embodiment.

The invention has been explained above with reference to the aforementioned embodiments. The invention is not only restricted to these embodiments, but comprises all possible embodiments within the spirit and scope of the inventive thought and the following patent claims. For example snap connector 102 as described in FIG. 4 is only a non-limiting example and can be replaced by other rigid component(s) 102, such as by way of non-limiting example only a transmitter, electrically conducting trace(s) and like printed wires.

In addition it is to be noted that it is beneficial in some embodiment that the material of the interface portion and/or first and/or second portions comprises some texture especially on the surface or the material structure is otherwise so that it comprises electrically conductive fibres or yarns interlacing with each other. This kind of structure enables living and tiny moving of the electrically conductive fibres or yarns in the structure against each other, thereby making the structure as durable as possible for bending, twisting and stretching, as well as ensuring good electrical contact and conductivity of the structure. Furthermore the interlacing structure of the electrically conductive fibres or yarns enables the electrically conductive fibres or yarns to penetrate e.g. thought adhesive thereby enabling electric contact between the interface portion and/or first and/or second portions.

The features recited in dependent claims are mutually freely combinable unless otherwise explicitly stated.

The invention claimed is:

1. A flexible or stretchable structural system for transmitting electrical signals between a first portion and a second portion, the system comprising:
a body structure and the first portion and the second portion arranged to the body structure, wherein
a modulus of elasticity of the first portion is lower than a corresponding modulus of elasticity of the second portion, and
a modulus of elasticity of the body structure is lower than a corresponding modulus of elasticity of the second portion, and
an interface portion arranged to the body structure, the interface portion electrically connecting the first portion and the second portion, and wherein a modulus of elasticity of the interface portion is lower than a corresponding modulus of elasticity of at least said the second portion,
wherein the first portion comprises electrically conductive first ink and the interface portion comprises electrically conductive second ink, where the second ink is at least one of more elastic, flexible, or stretchable than the first ink.

2. The system of claim 1, wherein the modulus of elasticity of the interface portion is lower than the corresponding modulus of elasticity of the first portion.

3. The system of claim 1, wherein said modulus of elasticity relates to the structure's resistance to being deformed elastically when a stress is applied to the structure, wherein the stress is at least one of flexibility or stretchability.

4. The system of claim 1, wherein the first portion comprises an electrically conductive trace, wherein the electrically conductive trace is at least one of a printed trace, a printed conductor, or an electrically conductive ink.

5. The system of claim 1, wherein the second portion comprises a printed circuit board, an electrical component, and a connector for connecting to the printed circuit board.

6. The system of claim 1, wherein the interface portion comprises at least one of an electrically conductive fabric, woven or knit fabric, textile, carbon nanotubes or polymer, Thermoplastic polyurethane (TPU), silicone, or electrically conductive ink.

7. The system of claim 1, wherein the body structure comprises a flexible substrate, the flexible substrate is at least one of textile, fabric, polymer, polyethylene terephthalate, or polyimide.

8. The system of claim 1, wherein the first portion and the second portion are one of physically separated portions or are physically connected to each other.

9. The system of claim 1, wherein the interface portion is arranged over the first portion and is connected by at least one of lamination, glue, printed, or molded.

10. The system of claim 1, wherein the interface portion is wider than the first portion.

11. The system of claim 1, wherein the interface portion is electrically coupled with at least one of the first portion or the second portion with an adhesive.

12. The system of claim 1, wherein the interface portion is selectively conductive, the interface portion further comprising at least one of embroidered conductive areas, conductive areas embroidered to the non-conductive fabric, conductive areas embroidered to a first cover portion, or conductive areas embroidered to a second cover portion.

13. The system of claim 1, further comprises a first cover portion and a second cover portion, wherein the first portion and the interface portion are arranged between the first cover portion and the second cover portion.

14. The system of claim 1, wherein the second portion is one of a snap connector or electrode punched through the body structure and the interface portion and arranged in connection with the first portion, and wherein the interface portion is configured to extend over the first portion.

15. The system of claim 14, wherein the second portion is punched through the interface portion.

16. The system of claim 15, further comprising a first cover portion, a second cover portion, and the second portion comprises a first snap connector portion and a second snap connector portion, wherein at least one of the first snap connector portion or the second snap connector portion is punched through at least one of the first cover portion or second cover portion in order to provide an electrode of the first snap connector portion or a connector stud of the second snap connector portion.

17. The system of claim 1, wherein the second portion is a seam between the first portion and another first portion, and wherein the interface portion is arranged to electrically couple the first portion and the another first portion over the seam.

18. A flexible or stretchable structural system for transmitting electrical signals between a first portion and a second portion, the system comprising:
    a body structure and the first portion and the second portion arranged to the body structure, wherein
        a modulus of elasticity of the first portion is lower than a corresponding modulus of elasticity of the second portion, and
        a modulus of elasticity of the body structure is lower than a corresponding modulus of elasticity of the second portion, and
    an interface portion arranged to the body structure, the interface portion electrically connecting the first portion and the second portion, and wherein a modulus of elasticity of the interface portion is lower than a corresponding modulus of elasticity of the first portion and the second portion.

19. A flexible or stretchable structural system for transmitting electrical signals between a first portion and a second portion, the system comprising:
    a body structure and the first portion and the second portion arranged to the body structure, wherein
        a modulus of elasticity of the first portion is lower than a corresponding modulus of elasticity of the second portion, and
        a modulus of elasticity of the body structure is lower than a corresponding modulus of elasticity of the second portion,
    an interface portion arranged to the body structure, the interface portion electrically connecting the first portion and the second portion, and wherein a modulus of elasticity of the interface portion is lower than a corresponding modulus of elasticity of at least the second portion, and
    a first cover portion and a second cover portion, wherein the first portion and the interface portion are arranged between the first cover portion and the second cover portion.

* * * * *